United States Patent [19]

Brentham

[11] Patent Number: 5,713,840
[45] Date of Patent: Feb. 3, 1998

[54] WEIGHTED LUMBAR SUPPORT

[76] Inventor: Jerry D. Brentham, 510 N. Loop 121, Belton, Tex. 76513

[21] Appl. No.: 534,549

[22] Filed: Sep. 27, 1995

[51] Int. Cl.$^6$ ........................... A61F 5/02
[52] U.S. Cl. ........................... 602/19; 128/96.1
[58] Field of Search ................ 602/19; 128/96.1, 128/99.1, 106.1, 112.1, 113.1, 120.1; 482/105; 2/92, 44, 250, 253

[56] References Cited

U.S. PATENT DOCUMENTS

| | | |
|---|---|---|
| 1,678,584 | 7/1928 | Branson . |
| 3,374,636 | 3/1968 | Mason . |
| 3,532,339 | 10/1970 | Smith . |
| 3,588,105 | 6/1971 | Donohoe . |
| 3,713,299 | 1/1973 | Duncan ................ 482/105 X |
| 3,735,598 | 5/1973 | Oeland, Jr. . |
| 3,888,245 | 6/1975 | Bernston et al. . |
| 3,924,851 | 12/1975 | Winston . |
| 4,099,524 | 7/1978 | Cueman et al. . |
| 4,180,261 | 12/1979 | Kolka . |
| 4,303,239 | 12/1981 | Walsh, Jr. . |
| 4,332,379 | 6/1982 | Banister . |
| 4,394,012 | 7/1983 | Egbert et al. . |
| 4,552,135 | 11/1985 | Racz et al. . |
| 4,570,619 | 2/1986 | Gamm . |
| 4,592,358 | 6/1986 | Westplate ............ 482/105 X |
| 4,674,664 | 6/1987 | Simon . |
| 4,768,499 | 9/1988 | Kemp . |
| 4,903,874 | 2/1990 | Shoemaker . |
| 4,936,495 | 6/1990 | Van de Pol . |
| 4,944,509 | 7/1990 | Snider . |
| 4,948,122 | 8/1990 | Andrews, Sr. . |
| 4,966,365 | 10/1990 | Winston ............ 482/105 |
| 5,067,484 | 11/1991 | Hiemstra-Paez . |
| 5,076,575 | 12/1991 | Eylander ........... 482/105 |
| 5,120,288 | 6/1992 | Sinaki . |
| 5,484,366 | 1/1996 | Wilkinson ......... 482/105 |
| 5,547,445 | 8/1996 | Chang ............... 482/105 |

FOREIGN PATENT DOCUMENTS

| | | |
|---|---|---|
| 218063 | 7/1967 | Sweden . |

OTHER PUBLICATIONS

HN Northern Summer Catalog #80, p. 142.

*Primary Examiner*—Jerome Donnelly
*Attorney, Agent, or Firm*—Crutsinger & Booth

[57] ABSTRACT

An apparatus and method of applying pressure to the lumbar region of a user wherein a lumbar support is secured to the back of a user and positioned and retained such that when the user is seated in a chair the lumbar support applies pressure to prevent realignment of the user's lower spine for maintaining proper posture. The lumbar support remains suspended so that it moves as the user moves, thereby retaining the lumbar support in a predetermined position relative to user's lumbar vertebrae. Weight in the lumbar support applies a moment to the spinal column to counterbalance the moment applied by extended arms or resulting from poor posture.

15 Claims, 2 Drawing Sheets

WEIGHTED LUMBAR SUPPORT

TECHNICAL FIELD

A weighted lumbar support secured about a user's back and positioned adjacent to lumbar vertebrae to apply pressure to the user's lumbar region during repetitive tasks and to counterbalance the weight of extended arms or a user's slumped posture and thereby reduce muscle tension and fatigue.

BACKGROUND OF INVENTION

The spinal column, composed of thirty-three vertebrae, is the major mechanical support for the human body. Each vertebrae has a short more or less cylindrical body, whose ends articulate by pads of elastic or cartilaginous discs with those of adjacent vertebrae, and a bony arch that encloses the spinal cord. A network of muscles supports the back like guy wires on a suspension bridge.

Improper alignment of the vertebrae resulting from improper posture unduly stresses muscles and "pinches" nerves. Eight out of ten cases of back pain can be traced to muscles, discs or joints. The result is neck pain and back pain that cause overall physical stress.

Back and neck muscles contract and relax during normal operation. However, under strain, an out-of-shape muscle can spasm, causing pain. The majority of back problems are muscle strains, brought on by people who do not exercise regularly attempting to perform activities that require strong muscles. The natural aging process wears down discs between the vertebrae, the vertebrae collapse and muscles tighten, causing a stooped-over posture.

A person's head, weighing about ten pounds and balanced on the end of the neck, has been compared to a bowling ball on a stick. Holding the head up requires effort to overcome the force of gravity. When standing or sitting, the head should be positioned such that the ears are above the shoulders to reduce muscle tension and fatigue.

The stomach muscles help hold up the back. A person with weak stomach muscles and a potbelly, which affects posture by straining the low back, is a prime candidate for back pain. Further, women with large breasts often suffer from muscle tension and fatigue, if their job requires sitting or standing all day typing, sewing, doing housework or performing other repetitive tasks.

To maintain the spinal column up-right, muscles must exert enough force pulling on the back in a clockwise direction to equal the sum of the forces pulling it in a counter-clockwise direction. For a static body, the sum of the moments about an axis is equal to zero, where "moment" is defined as the product of the magnitude of force and the distance to the particular axis. Muscles tire quickly during any activity that involves the use of the hands and arms extended in front of the body, such as mowing grass or preparing meals.

Good posture, which helps a person use proper body mechanics, aids in preventing repetitive muscle strain in the upper back, neck and shoulders. When a person stands or sits with arms and hands extended any length in front of them, their line of gravity moves forward. The muscles in their upper back try to keep their shoulders from rotating forward. Over a period of time these muscles tire and pain occurs.

Repetitive strain injuries are commonplace to workers who regularly use computers or work on assembly lines. Repetitive strain injuries generally include various nerve, tendon and muscular disorders. Although symptoms vary, the repetitive action of typing on computer keyboards can damage sensitive tissues in hands, shoulders and wrists that can cause pain, numbing and loss of motor control. It has been proposed that work stations be redesigned to provide adjustable work space with ergonomically designed chairs having height adjustments and articulating seats and backs to keep the body of the user properly positioned as he or she moves. It has also been proposed that such chairs be provided with a contoured seat to distribute body weight evenly and minimize pressure under thighs to promote proper blood circulation. Further, it has also been proposed that the chair be provided with a flexible back that conforms to the natural contour of the spine for providing support.

When a person types or performs similar repetitive tasks over a long period of time, stomach and back muscles tire causing the person to lean or slump forward. Improper posture often results in excessive physical stress. Such stress may cause the person to suffer from chronic, unexplained stiff neck, headaches, backaches, and intestinal or stomach upsets. Clenching or grinding teeth, flushing or perspiring more than usual are also considered symptoms of excessive stress. Further, increased drinking, smoking or self-medicating with over-the-counter tranquilizers or sleeping aids may also be observed.

Another example of the severe symptoms accompanying repetitive strain injuries is a condition referred to as carpal tunnel syndrome. This condition is thought to be unnecessarily suffered by many who work at computer terminals or assembly line work stations. The repetitive wrist motion required when keying in data, while leaning on the arms and hands on the edge of a typing desk, causes the median nerve in the hand to rub against a narrow space in the carpal tunnel space in the underside of the wrist. This repetitive motion damages the nerve and causes tingling, numbness or pain in the thumb, index finger, middle finger and ring finger. It has been proposed that wrist rests be provided to prevent carpal tunnel syndrome and increase comfort and productivity by elevating the wrist. A padded wrist rest for supporting the hands about 26 inches from the floor keeps the wrist straight thereby reducing wrist motion and pressure on the median nerve while typing or keying data. Placing a keyboard a working height of 29 to 30 inches and resting the hands and arms on a hard surface greatly increases the risk of musculoskeletal problems, ranging from discomfort to disabling injury of the wrist, arm, shoulder and neck.

U.S. Pat. No. 5,067,484 and U.S. Pat. No. 5,120,288 disclose a therapeutic device for use by a therapist in a clinical setting for posture training treatment. These devices incorporate a pouch with adjustable clavicle straps sized for positioning a weight on the back of a patient just below the inferior angle of the patient's scapulae. The device is designed to lie against the upper back of the patient, with the length of the weight pouch running parallel to the patient's spinal column. The disclosures of these two patents appear to be substantially identical to each other and explain that positioning a weight on the upper portion of the patient's back, between the shoulder blades, is a biomechanical approach to appropriately position a weight to counteract the patient's tendency to stoop forward. The patents state that in use, an appropriate combination of weights is selected by the treating physician to treat a specific patient. Individual weights are secured in weight pockets, in lieu of devices such as thoracolumbar supports and shoulder orthoses generally used for treatment of posture disorders.

SUMMARY OF INVENTION

The lumbar support of the present invention is designed to be suspended from the shoulders and nestle in the user's lumbar region when the user is standing or seated. Also, the present invention is designed such that lumbar support rolls carrying weights extend transversely behind the spinal column of the user for support of the lumbar region and for exerting gravitational force to urge the spinal column toward and up-right position.

The weighted lumbar support disclosed herein is a device to be worn by a user to prevent muscle tension and to reduce stress often caused by repetitive tasks while in either in a standing or sitting position.

A lumbar support having a predetermined rectangular size and shape is suspended by adjustable shoulder straps such that the lumbar support is positioned adjacent the lumbar region of the user to prevent realignment of the user's lower spine of the user and to maintain proper posture when the user is seated in a chair. This lumbar support relieves muscle tension otherwise generated by an unsupported user's effort to maintain proper sitting or standing posture. Further, suspending the lumbar support from the user's body causes the lumbar support to conform to the natural contour of the user's spine. This act supports the user's lower back with optimal comfort while the lumbar support is maintained in the desired position in the lumbar region of the back as the user twists, turns or otherwise moves while in a seated or standing position.

In a preferred embodiment of the invention the lumbar support is formed by lumbar rolls suspended by intersecting or non-intersecting straps. The resulting downward force caused by the weighted lumbar support counteracts a user's tendency to slump or stoop as the weight of body parts of the user projecting from the torso. A horizontal force component also exists which maintains the weighted lumbar support in the user's lumbar region. Additional pressure to the user's lumbar region results when the user is seated in a chair with a back.

Providing the combination of a lumbar support adjacent the small of the back of the user and as the user reaches forward, the properly positioned lumbar support counterbalances the moment created by the user's reaching action. This counterbalancing also reduces the tendency of the user to stoop or slump forward while performing repetitive tasks in a seated or a standing position. Further, the lumbar support and counterweight move with the user without interfering in any way with activities to be performed by the user.

The specific shape and configuration of the apparatus for suspending the weighted lumbar support in the desired position may vary depending upon the activities to be performed and the desire of the user. For example, a male user may prefer that the weighted lumbar support be suspended from shoulder straps or suspender-like straps which connect to the waistband of a pair of trousers with the straps configured in an intersecting or non-intersecting fashion. A female user might prefer a smock or vest having the weighted lumbar support mounted therein to provide a more pleasant appearance and to eliminate any possibility that clips on suspenders might snag, wrinkle or otherwise damage delicate articles of clothing. It should be readily apparent that the weighted lumbar support may be worn under or over clothing or incorporated in a garment to provide alternate methods for positioning and retaining the lumbar support.

DESCRIPTION OF DRAWINGS

Drawings of a preferred embodiment of the weighted lumbar support are annexed hereto so that the invention may be better and more fully understood, in which.

Other objects and advantages of the invention will become apparent upon reading the following detailed description and upon reference to the drawings, in which like reference numerals are used throughout the drawings to designate like parts.

DESCRIPTION OF A PREFERRED EMBODIMENT

Figure 1:
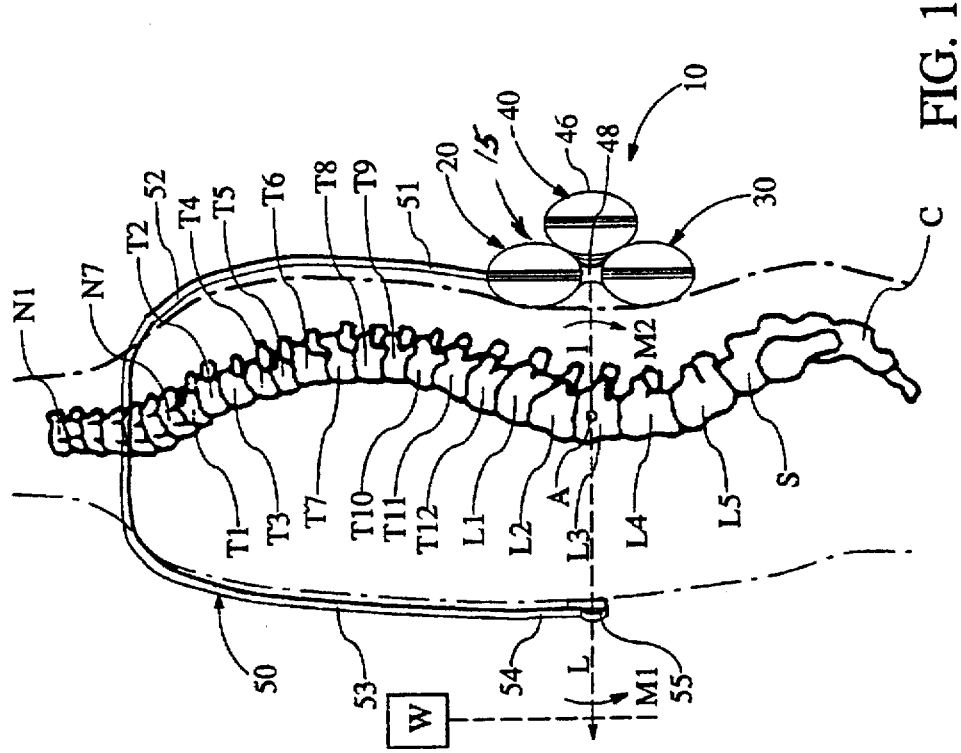
FIG. 1 is a diagrammatic view of the weighted lumbar support positioned adjacent the lumbar region of a human body.

The vertebral column or backbone in humans is composed of thirty-three vertebrae. Referring to FIG. 1, the human backbone consists of seven cervical N1–N7, twelve thoracic T1–T12, five lumbar L1–L5, five sacral S1–S5 and four coccygeal C1–C4 vertebrae. The lumbar vertebrae L1–L5, in the small of the back, extend to the articulation of the pelvic girdle, where a fused series of vertebrae constitutes the sacrum. The small of the back is referred to herein as the lumbar region.

Referring to FIG. 1 of the drawing, the lumbar support 10 of the present invention has a first lumbar roll 20 and a second lumbar roll 30, forming a primary lumbar support 15, and an auxiliary lumbar roll 40. The primary lumbar support 15 is suspended from the shoulders by any suitable suspension mechanism that will position it adjacent the lumbar region of the back and apply a moment in a clockwise direction, as viewed in FIG. 1. In the embodiment illustrated in FIG. 1, lumbar rolls 20 and 30 are supported by ends 51 of portions 52 of straps 50. Portions 52 of straps 50 extend up the back and over the shoulders and portions 53 extend downwardly from the shoulders.

Portions 53, in the embodiment of FIG. 1, are similar to the front portion of a pair of conventional suspenders, extending downwardly and connected to a waist band to support trousers, a skirt or belt. Suitable connectors 55, such as clips, belt loops or straps having button holes, are secured to ends 54 of portions 53 of each strap 50.

If each lumbar roll 20, 30 and 40 weighs, for example one pound, and is positioned such that the center of gravity of the combined device is a distance "l" of one foot from a horizontal axis A extending through the spinal column, a moment M2 is applied in a clockwise direction as view in FIG. 1 of the drawing by the lumbar rolls.

The weight W, in FIG. 1 of the drawing, represents the weight of hands and arms extended outwardly in front of the spinal column a distance L. It should be readily apparent that this applies a moment M1 in a counter-clockwise direction about the horizontal axis A that is equal to the weight W times the length L.

Force exerted by muscles for supporting the spinal column is equal to the difference in the moment M1 and the moment M2 since the moments M1 and M2 about axis A are in opposite directions. If lumbar rolls 20, 30 and 40 were not applying the moment M2, the muscles of the body would be required to exert sufficient force to overcome the entire moment M1.

Various embodiments of the apparatus are illustrated in FIGS. 1, 2, 3 and 4 of the drawing.

As hereinbefore described, in the embodiment of FIG. 1, ends 54 of straps 50 are provided with connectors 55 that are secured to a belt or clothing worn by the user.

Figure 2:
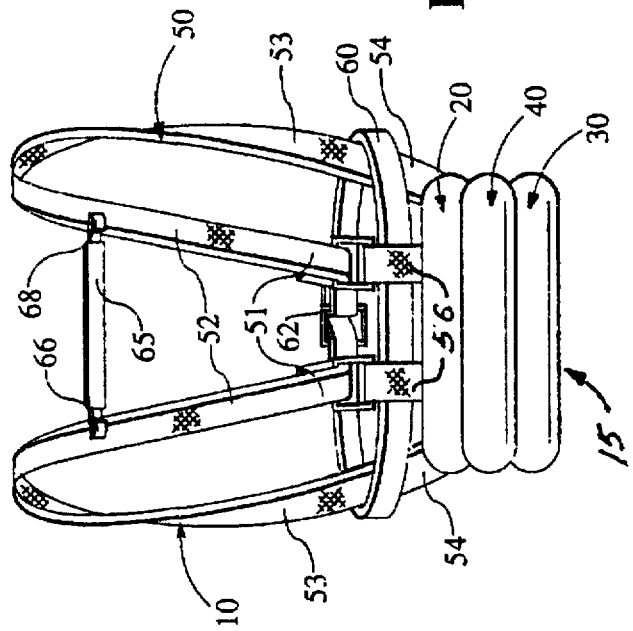
FIG. 2 is a rear elevational view of a second embodiment of the weighted lumbar support.
Figure 3:
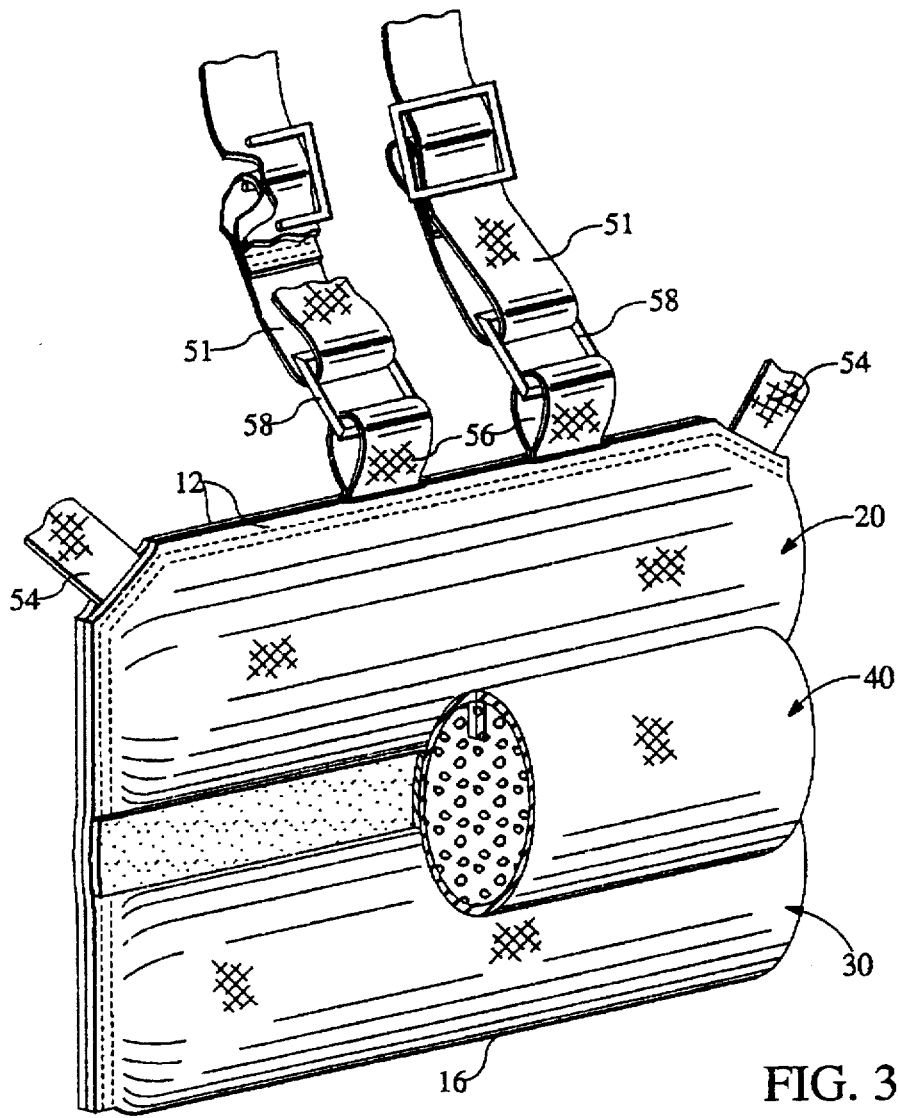
FIG. 3 is a enlarged perspective view of primary and auxiliary weighted lumbar supports.

In the embodiment of FIGS. 2 and 3 of the drawing, ends 54 of straps 50 are secured to ends of the first lumbar roll 20, for example by attaching connector 55 to lumbar roll 20 or by otherwise securing ends 54 of straps 50 thereto. A belt 60 secures ends 51 and 54 of straps 50 so that lumbar rolls 20, 30 and 40 will not slide from side to side if the person wearing the device is bending, lifting or otherwise moving or working around machinery.

Figure 4:
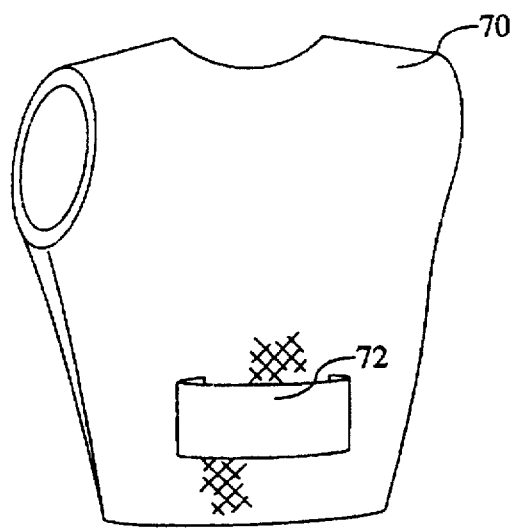
FIG. 4 is a rear elevational view of a third embodiment the of a weighted lumbar support mounted on a garment of clothing.

In the embodiment of FIG. 4, lumbar rolls 20, 30 and 40 are positioned in a pocket 72 formed in or on a garment, such as a vest 70.

Lumbar rolls 20, 30 and 40 are similarly constructed in each of the embodiments of FIGS. 1, 2, 3 and 4.

The lumbar rolls 20, 30 and 40 are preferably made of a soft, durable and slightly elastic encasement material 42, such as velour fabric with a pile or nap surface resembling velvet, a soft pliable vinyl plastic, leather or other suitable material.

The primary lumbar support 15 includes first and second lumbar rolls 20 and 30. The primary lumbar support 15 may be formed by folding a rectangular piece of flexible encasement material 42 for forming a bottom edge 16 and two top edges 12, as illustrated in FIG. 3 of the drawing. A strip 35 of hook/loop connector material is sewn along an edge thereof by one or more lines 32 of stitching to form a cylindrical encasement below strip 35. The upper edge of strip 35 is secured by one of more rows 26 of stitching for forming the lower portion of a generally cylindrical encasement for roll 20.

In the embodiment illustrated in FIG. 3 of the drawing, loops 56 extend through links 58 and opposite ends of each loop 56 are positioned between top edges 12 of encasement material 42. One or more rows 22 of stitching are formed adjacent top edges 12 of encasement material 42 for forming a seam along the upper edge of primary lumbar support 15 and for securing loops 56 to the primary lumbar support 15.

In the illustrated embodiment, ends 54 of shoulder straps 50 are positioned between top edges 12 of primary lumbar support 15 and are secured thereto by one or more rows 24 of stitching adjacent opposite ends of the first lumbar roll 20. It should be appreciated that rows 22 and 24 of stitching are positioned to form a continuous seam along the upper edge of lumbar roll 20 for securing opposite ends of shoulder strap 50 to the primary lumbar support 15.

Vertical rows 26 of stitching close opposite ends of lumbar rolls 20 and 30 after they have been filled with a suitable filler material 44, such as granular coal, metallic spheres or other material having sufficient density to provide the desired weight. However, the material should be deformable such that the primary lumbar support 15 is deformable to fit the contour of the back of the user and pliable such that it does not feel too hard when a user is seated in a chair having a back.

The auxiliary lumbar roll 40 is formed by folding a piece of encasement material to form a lower edge 46 and top edges 42. Top edges 42 are connected by a row of stitching for forming a cylindrical body. A strip 46 of hook/loop connector material is sewn onto the outer surface of auxiliary lumbar roll 40. Strips 35 and 36 of hook and loop connector material detachably secure the auxiliary lumbar roll 40 between primary lumbar rolls 20 and 30 of the primary lumbar support 15. After the auxiliary lumbar roll 40 has been filled with particulate material 44 the upper edges 42 are secured together by a row of stitching (not shown) and opposite ends are closed by rows of stitching.

Ends 51 of shoulder straps 50 extend through links 58 that are secured by loops 56 to a central portion of lumbar roll 15.

Ends 51 of shoulder straps 50 preferably have buckles 50a mounted as illustrated in FIG. 3 of the drawing. Buckle 50a can be moved longitudinally of portion 52 of shoulder strap 50 for adjusting the length of each shoulder strap 50 for positioning the primary lumbar support 15 in the lumbar region of the back.

As illustrated in FIG. 2 of the drawing, a belt 60 having a buckle 62 may be positioned to extend through loops 56 and around portions 53 of shoulder straps 50 to assure that the primary lumbar support 15 does not swing or move laterally.

A horizontally extending connector strap 65, having clips 66 and 68 on opposite ends thereof connectable to portions 52 of shoulder straps 50, is provided to assure that shoulder straps 50 do not slide off of the shoulders of the user.

It should be appreciated that other and further structures may be used for positioning primary lumbar support 15 and auxiliary lumbar roll 40 adjacent the lumbar region of the back of the user. As illustrated in FIG. 4 of the drawing, a garment 70 having a pocket 72 formed thereon may be positioned to receive lumbar rolls 20, 30 and 40. Pocket 72 preferably is closed at the bottom and a zipper, snaps or other closures may be used across the upper end of pocket 72.

Positioning the lumbar support 10 as illustrated in FIG. 1 of the drawing, applies a physical moment M2 counterbalancing the moment M1 as hereinbefore described. In addition, force exerted by portion 52 of shoulder straps 50 or by garment 70 gently tugs rearwardly on the shoulders of the user to provide feedback to the user. This sensory feedback reminds the user that he should maintain good posture.

It appears that positioning the primary lumbar support 15 at a higher elevation, for example in the vicinity of thoracic vertebrae T4 and T5 results in movement of the center of gravity of the primary lumbar support 15 past the axis A, illustrated in FIG. 1 of the drawing, which would cause the moment M2 to act in the opposite direction which could result in an increase in muscle tension and fatigue. Thus, it is important that the primary lumbar support 15 be properly positioned to provide the desired results.

The first lumbar roll 20 and the second lumbar roll 30 are sized to fit within the lumbar curve of a person's back. The first lumbar roll 20 and the second lumbar roll 30 have lengths in a range between about 8 and 12 inches and a height in a range between about 2 to 6 inches. A preferred length is about 10 inches and a preferred height of the primary lumbar support 15 is about 4 inches. The first lumbar roll 20 and the second lumbar roll 30 have a combined weight in a range between about 2 and 6 pounds. A preferred weight of the primary lumbar support 15 is about 2 pounds.

The auxiliary lumbar roll 40 preferably has a length in the range between about 8 and 12 inches and a height in a range between about 2 and 6 inches. A preferred length is about 10 inches and a preferred height is about 2 inches. The weight of the auxiliary lumbar support is in the range between about 1 to 2 pounds. A preferred weight is about 1 pound.

As shown in FIG. 3, the auxiliary lumbar roll 40 is connected to the concave depression 17 between the first lumbar support 20 and the second lumber support 30 by a hook/loop connector 35 and 36. A preferred hook/loop connector is commercially available under the trademark "VELCRO." The separate hook and loop components of the hook and loop connector may be used interchangeably. The hook portion 35 may be mounted lengthwise on the auxiliary inner face 36 and the mating loop portion 36 of the connector may be mounted in the concave depression 17 formed between first lumbar roll 20 and second lumbar roll 30. With this method of connection, ready adjustment of the overall weight of the lumbar support 10 is made according to the weight and build of the user of the lumbar support 10.

As shown in FIG. 2, the first ends 52 of shoulder straps 50 are attached to links 58 which are in turn attached to loops 56 which are in turn incorporated into the upper seam 22 of the first lumbar roll 20. In a preferred embodiment, the second ends 54 of the should straps 50 are also incorporated into the upper seam 22, forming a loop to fit over the user's shoulders. The straps 50 are adjustable to a sufficient length to accommodate different user's lumbar regions.

The lumbar support 10 is worn by a user by inserting their arms through the loops formed by straps 50, so that the straps 50 are placed over the shoulders of the user. The lumbar support 10 is properly positioned preferably within the lumbar region of a user's spine (see FIG. 1). Such positioning is achieved by adjusting the lumbar support 10 to accommodate the size of the particular user through the adjustability of the straps 50. As the lumbar support 10 is secured about the shoulders of a user, it is then positioned and retained on the back of the user adjacent lumbar vertebrae of the spinal column such that when the user is seated in a backed chair, the lumbar support 10 applies pressure to the lumbar region to prevent realignment of the lower spine of the user and for maintaining proper posture. As the user moves, the lumbar support 10 moves such that the lumbar support 10 is retained in the user's lumbar curve. Furthermore, as the user reaches forward, the properly positioned lumbar support 10 counterbalances the moment created by the user's reaching action. This kind of balance helps equalize the center line of gravity in the upper torso, thereby relieving some of the muscle strain.

The straps 50 are adjustable to allow for a more comfortable fit to the body structure. The middle auxiliary roll 40 and weight is removable enabling use of a two or three pound counter-balance.

The lumbar support 10 is held in left hand with the adjusting buckles 50a and the auxiliary roll 40 facing away from user, preparatory to putting it on the back. The user should Insert the right hand in the loop of the shoulder strap 50 closest to the left thumb. He then pulls the shoulder strap up onto right shoulder. He should then hook his right thumb into the loop formed by the left shoulder strap and pull the left shoulder strap with his right hand over-head and insert his left arm into the loop formed by the left shoulder strap. After both arms are in the loops formed by the shoulder straps 50, the user should make certain that the straps are straight.

The lumbar support was designed and developed to aid people with shoulder and upper back strain while working at their different professions. It should be worn while working but it is very beneficial while engaging in any activity that involves the use of the hands and arms extended in front of the body, such as sewing, painting, mowing or preparing meals.

For women under 140 pounds, it is recommend that the two pound primary lumbar support be used initially. Wear it for 30 minutes to an hour and add the one pound auxiliary roll 40 if needed.

For women over 140 pounds, it is recommend that the two pound primary lumbar support rolls 20 and 30 with the one pound auxiliary roll 40 attached be worn for 30 minutes to an hour. If the user begins to feel fatigue or discomfort, the one pound auxiliary roll 40 and weight can be removed.

It is recommended that men, start with the 3 lb. unit. If after a short period of time he feels that it is too heavy, he should take off the one pound auxiliary roll 40. If the three pound unit feels is too light, the user should not concerned, because the lumbar support is doing it's job.

The first time the lumbar support is used, the user should try to wear it for over two hours. He should then take the unit off completely and let his body rest. If the user should feel discomfort or fatigue during or after wearing the lumbar support, he should not be discouraged, because it will take some time for his body to adjust. Some people are able to wear the unit for extended periods of time while others need to take it off throughout the day. The body will let the user know which is best for his, but it is recommended that for initial use, the user wear it about two hours and take it off for 30 minutes to an hour.

Experiments have been conducted to compare the moments of force, the muscular force exerted by the erector spinae muscles, and the compression and shearing forces exerted on the spinal column when subjects were performing simple tasks while wearing and not wearing the lumbar support.

The basic task was to try and determine if the lumbar support had potential for preventing or relieving the apparent symptoms of muscular strain and discomfort by measuring appropriate parameters (moments of force, muscular force, and compression and shearing forces) at three regions along the spinal column (upper spine, mid-spine and lower spine). To try and determine these effects, subjects performed simple tasks under two experimental conditions. In the first condition, subjects would wear the lumbar support. In the second condition, subjects would perform the same manual tasks without the lumbar support. If there was going to be a positive effect of wearing the lumbar support, then for a subject who wears the lumbar support, there should be less muscular and shearing forces on the spine compared to when the subject did not wear the lumbar support. Even a small difference between experimental conditions of one or two percent per minute in favor of the lumbar support would translate into considerable "savings of muscular strain and discomfort" when the lumbar support is worn during a typical work day of 480 minutes.

In designating the experiment, it was important to accomplish two things: (1) to mimic a real life situation for the experimental tasks, and (2) to obtain enough information from "normal" subjects (i.e., subjects who were free of existing back pain and subjects with no back abnormalities such as scoliosis) to permit statistical analysis of the two experimental conditions (wearing the lumbar support versus not wearing the lumbar support). Another important consideration was to evaluate the subjects while wearing and not wearing the lumbar support as they performed the tasks at an extreme of forward trunk flexion (45 degrees). This was done to provide an upper range of values for calculating moments of force, muscular force, and compression and shearing forces.

Ten males and ten females volunteered to participate in the study. They ranged in age from 18 to 51 years, with an average of 32.5 years. No subject was tested who had an existing back problem or an existing back condition such as scoliosis or a congenital spinal defect. The subjects represented "average" individuals from the surrounding neighborhoods. None of the subjects were currently in training for a competitive sport (such as a marathon or triathlon).

The duration of each training session lasted approximately 30 minutes and involved four treatment conditions:

(1) wearing the lumbar support while seated, (2) wearing the lumbar support while standing up, (3) not wearing the lumbar support while seated, (4) not wearing the lumbar support while standing up.

A wooden cardboard (37 cm×55 cm) containing nine peg holes (7.5 cm diameter) was used to perform the experimental task. The position of the cardboard varied according to the height of the subject and the experimental condition (seated or standing up). The top of the cardboard was kept at eye level for each subject. The distance between the subject and the cardboard could be adjusted so that when the subject stood erect, their fingers could touch the most distant peg hole. Once the pegboard was positioned properly, the subjects were not to move their feet (while in the standing position) or their hips (while in the seated position) performing the task. Each subject was instructed to bend at the trunk or flex at the knees (while standing) while performing the task. A screw driver and hair dryer (each with weight added to the final weight was 2 kg (4.4 lbs.) were placed in two of the peg holes. The task was to move the object clockwise from peg hole to peg hole, take one object out of the hole and replacing it with the other object, and so on, for a total of five minutes. This task was repeated for each of the four experimental conditions. The objects were moved from hole to hole in a deliberate manner, without trying to "hurry." A video system (32 frames per second) was used to film the subjects during the four experimental conditions. A computerized data analysis system with a Graph-pen digitizer was used to acquire the following criterion measurements directly from the film: (1) forearm and hand segment position, (2) upper arm position, and (3) trunk position.

These data were subsequently used to calculate the following parameters using analytical procedures described in detail by Plagenhoef, S.: *Patterns of Human Motion.* Prentice-Hall, New York, 1971 and Hayes, K., and Wood, G.: A kinetic model of intervertebral stress; proceedings of Canadian Society of Biomechanics, 1973:

1. Moments of force (expressed in newton.meters (N.m) at each of the following five joints: elbow, shoulder, T5–T6 (level of mid-scapula), T10 (level of tip of xiphoid process; bottom of sternum) and L5–S1 (lower back).

2. Estimates of the muscular force exerted by the erector spinae muscles (expressed in N), intervertebral compression forces (Fc; expressed in N), and shearing forces (Fs; expressed in N) at each of the spinal levels (T5–T6, T10 and L5–S1).

There were two basic statistical approaches of statistical analysis. The first analysis compared the seated and standing experimental conditions. The results of this analysis showed there were no significant differences among the two seated and standing positions (P>0.05); thus, only the experimental condition involving standing was retained for further analysis.

The second analysis consisted of a comparison of the average segmental position of the trunk while subjects performed the experimental tasks with and without the lumbar support. Because there was a significant difference in trunk position (p<0.01), the subsequent analysis compared all of the force measurements between the two trunk positions (10 degrees of forward trunk flexion vs. 20 degrees of forward trunk flexion; including a comparison at 10° of forward trunk flexion, and the extreme position of 45° of forward trunk flexion.

Results were analyzed for moments of force, muscular force exerted by the erector spinae, and compression (Fc) and shearing forces (Fs) for trunk flexion at 10 degrees while wearing the lumbar support, and for trunk flexion at 20 degrees without wearing the lumbar support. It was observed that when the subjects did not wear the lumbar support, their trunk was flexed 20 degrees of forward flexion. When the subject wore the lumbar support, their trunk was flexed to only 10 degrees of forward flexion.

This indicates that wearing the lumbar support forced the subjects to keep their trunks in a more upright position (10 degrees of forward flexion) compared to when they did not wear the lumbar support (20 degrees of forward flexion). It is evident from the analysis that the largest effect is in the upper back region compared to the mid-back and lower back regions, and the effect of wearing the lumbar support makes the subject assume a better posture, thereby reducing the total forces on the spine (including the muscular and shearing forces).

The results of the experiment show that one of the features of the lumbar support is that users maintain their back more upright when they wear the lumbar support compared to when they do not wear it. There was no question that the subjects using the lumbar support executed the experimental task with their trunk flexed at 10 degrees. In contrast, when subjects performed the same experimental tasks without the lumbar support, they flexed their trunk at 20 degrees of forward flexion. In addition, there was significantly less force exerted at the upper spine compared with the mid-spine and lower spine areas when subjects wore the lumbar support than when they did not wear the lumbar support. Considered together, the shearing and compressive forces were reduced in the upper back region by up to 7.5% when subjects wore the lumbar support.

The lumbar support seems to exert a positive effect on muscular forces (including compression and shearing forces). The lumbar support provides the brain with important sensory feedback information that cues a person to assume a better posture while performing normal daily life activities. The cumulative effect of wearing the lumbar support reduces the magnitude of forces along the spine, with the largest effects prevalent in the upper back and lower shoulder region.

Having described the invention, I claim:

1. A weighted lumbar support for applying force to the lumbar region of a subject for reducing muscle tension and fatigue comprising:

an elongated, generally horizontally extending, primary lumbar support filled with granular material, said lumbar support having horizontally spaced end portions;

a pair of shoulder straps having first and seconds ends;

means securing first ends of each of said shoulder straps to a central portion of said primary lumbar support; and means securing second ends of said shoulder straps to said horizontally spaced end portions of said primary lumbar support such that said straps are positionable to extend around shoulders of the subject for positioning said primary lumbar support to engage the lumbar region of the subject, said granular material having a weight of at least two pounds and not more than five pounds for applying force to shoulders of the subject for exerting a moment on the spinal column for counter-balancing a portion of the moment exerted on the spinal column by body parts extending forwardly from the spinal column, wherein said primary lumbar support has a length, measured horizontally, in a range between 8 and 12 inches and a height in a range between 2 and 6 inches.

2. A lumbar support for applying force to the lumbar region of a subject for reducing muscle tension and fatigue according to claim 1, with the addition of a belt secured to said shoulder straps positionable around the waist of the subject for preventing movement of said primary lumbar roll relative to the lumbar region of the back when the subject bends, lifts or moves.

3. A lumbar support for applying force to the lumbar region of a subject for reducing muscle tension and fatigue according to claim 1, with the addition of a connector strap secured between central portions of said shoulder straps to prevent the shoulder straps from slipping off of shoulders of the subject.

4. A weighted lumbar support configured to be worn by a subject comprising:

a first lumbar roll and a second lumbar roll each having an elliptical cross-section, said second lumbar roll connected lengthwise beneath said first lumbar roll such that between said first and second lumbar roll a concave depression is created;

an auxiliary lumbar roll having an outer face and an inner face with an elliptical cross-section for adding weight to said first and second lumbar rolls;

a hook and loop connector with a hook portion and a loop portion used interchangeably, said hook portion secured to the concave depression formed between said first and second lumbar roll for mating with said loop portion connected to said inner face of said auxiliary lumbar roll; and at least a pair of adjustable shoulder straps of sufficient length with each strap having a first and second end attached to said first lumbar roll on opposing halves of said first lumbar roll for positioning said first and second lumbar roll about said lumbar vertebrae of said subject.

5. A weighted lumbar support as recited in claim 4, wherein said first and second lumbar roll each have an individual length in a range of between eight and twelve inches and each have an individual height in a range between two and six inches.

6. A weighted lumbar support as recited in claim 4, wherein said first and second lumbar roll has a weight in a range between one and three pounds and the weight of said auxiliary lumbar roll being in a range between one and two pounds.

7. A weighted lumbar support as recited in claim 4, wherein said adjustable shoulder straps have said first ends attached adjacently about the vertical moment of said first lumbar roll and with said second ends attached to opposing edges of said first lumbar roll such that said shoulder straps do not intersect.

8. A weighted lumbar support as recited in claim 4, wherein said adjustable shoulder straps have said first ends attached adjacently about the vertical moment of said first lumbar roll and with second ends attached to opposing edges of said first lumbar roll such that said straps intersect.

9. A weighted lumbar support as recited in claim 4, wherein said adjustable shoulder straps have said first ends attached adjacent about the vertical moment of said first lumbar roll and said second ends terminating in clips for securing said second ends to clothing.

10. A weighted lumbar support configured to be worn by a subject comprising:

a first lumbar roll and a second lumbar roll each having an elliptical cross-section, said second lumbar roll connected lengthwise beneath said first lumbar roll such that between said first and second lumbar roll a concave depression is formed;

at least one auxiliary lumbar roll having an elliptical cross-section;

means for detachably securing said auxiliary lumbar roll within the concave depression formed between said first lumbar roll and said second lumbar roll; and adjustable strap means of sufficient length for suspending said lumbar support such that said lumbar support may be positioned for retaining said lumbar support in a predetermined position relative to lumbar vertebrae of said subject.

11. A weighted lumbar support as recited in claim 10, wherein said first and second lumbar roll each have an individual length in a range of between eight and twelve inches and each an individual height in a range between two and six inches.

12. A weighted lumbar support as recited in claim 11, wherein said combined weight of said first and second lumbar roll has a weight in a range between two and six pounds and the weight of said auxiliary lumbar roll being in a range between one and two pounds.

13. A weighted lumbar support as recited in claim 12, wherein said adjustable means comprise a pair of adjustable shoulder straps with first and second ends, said first ends attached adjacently about the vertical moment of said first lumbar roll and said second ends attached to opposing edges of said first lumbar roll such that said straps do not intersect.

14. A weighted lumbar support as recited in claim 12, wherein said adjustable means comprise a pair of adjustable shoulder straps with first and second ends, said first ends attached adjacently about the vertical moment of said first lumbar roll and said second ends attached to opposing edges of said first lumbar roll such that said straps intersect.

15. A weighted lumbar support as recited in claim 12, wherein said adjustable means comprise a pair of adjustable should straps with first and second ends, said first ends attached adjacently about the moment of said first lumbar roll and said second ends terminating in clothing clips for securing said second ends to clothing.

* * * * *